United States Patent [19]

Goosen

[11] Patent Number: 5,019,060
[45] Date of Patent: May 28, 1991

[54] DRAINAGE BLOOD COLLECTION APPARATUS

[76] Inventor: Carl C. Goosen, 2415 Shoreham Rd., Orlando, Fla. 32803

[21] Appl. No.: 308,540

[22] Filed: Feb. 10, 1989

[51] Int. Cl.$^5$ ............................................. A61F 5/44
[52] U.S. Cl. ...................................... 604/319; 604/321
[58] Field of Search .............................. 604/317–326

[56] References Cited

U.S. PATENT DOCUMENTS

| | | | |
|---|---|---|---|
| 3,861,390 | 1/1975 | Schachet | 604/321 |
| 4,015,603 | 4/1977 | Kurtz et al. | 604/321 |
| 4,265,243 | 5/1981 | Taylor | 604/325 |
| 4,430,085 | 2/1984 | Ahrens | 604/321 |
| 4,439,189 | 3/1984 | Sargent et al. | 604/321 |
| 4,439,190 | 3/1984 | Protzmann et al. | 604/319 |
| 4,533,353 | 8/1985 | Akiyama | 604/321 |
| 4,704,106 | 11/1987 | Shave et al. | 604/321 |
| 4,715,856 | 12/1987 | Elliot et al. | 604/321 |
| 4,838,872 | 6/1989 | Sherlock | 604/321 |

FOREIGN PATENT DOCUMENTS 8403838 10/1984 PCT Int'l Appl. ............... 604/321

Primary Examiner—Stephen C. Pellegrino
Assistant Examiner—Ralph A. Lewis
Attorney, Agent, or Firm—A. W. Fisher, III

[57] ABSTRACT

A liquid collection device for use with various surgical procedures to control and monitor the rate of flow of liquid from one or more body cavities such as the pleural and/or mediastinal cavities comprising a liquid collection section including an upper liquid flow rate monitoring chamber coupled to the body cavity by a fluid conduit to receive a predetermined volume of fluid to a lower liquid accumulation reservoir when the predetermined volume of liquid is received therein and a pressure control/liquid isolation section coupled to a vacuum source to control the flow of liquid from the body cavity through the fluid conduit at a predetermined pressure.

20 Claims, 4 Drawing Sheets

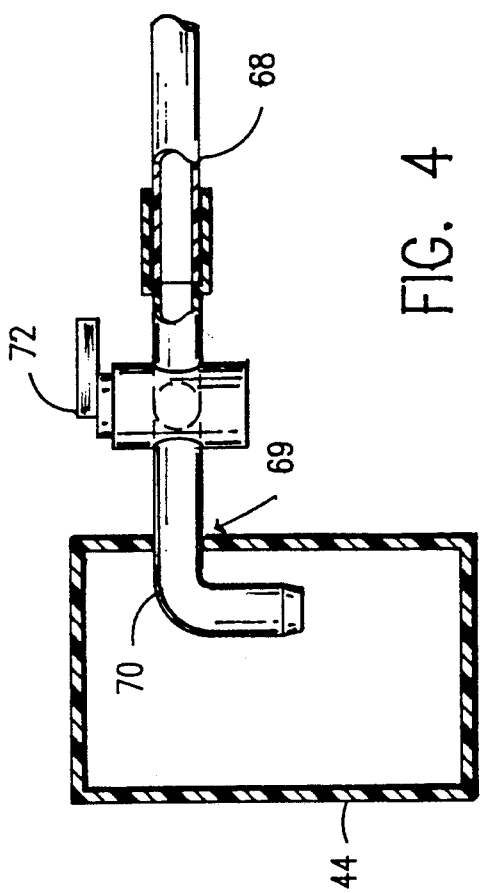
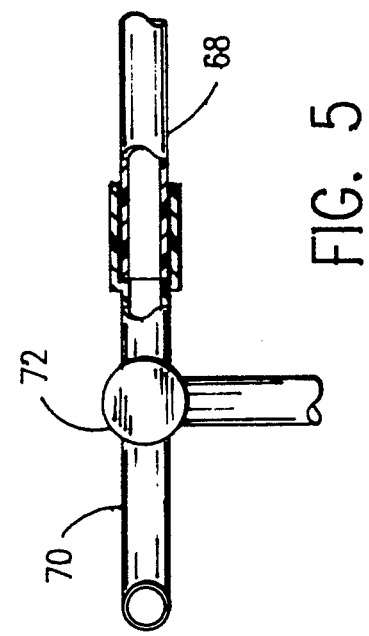

DRAINAGE BLOOD COLLECTION APPARATUS

BACKGROUND OF THE INVENTION

1. Field of the Invention

A liquid collection device for use with various surgical procedures to control and monitor the rate of liquid flow from one or more body cavities.

2. Description of Prior Art

Various devices have been developed to collect and monitor blood loss from mediastinal and pleural drainage after cardiac and other thoracic surgery. Accurate monitoring of these blood losses is essential to determine the necessity for blood replacement. To insure an accurate measure, it is important that blood not accumulate in the patient long enough to clot and thereby distort actual blood loss.

Generally systems currently in use permit blood clotting in the mediastinal and pleural areas. This is particularly dangerous in patients with "whole blood" bleeding.

Blood clotting normally results from the failure to properly drain due to the geometry of the drainage tube between the catheter or catheters and the collection device. The drainage tube is usually a soft latex tube having a relatively large bore. The large bore is mistakenly thought to promote easier flow for the drainage components. The soft latex enables stripping or milking to facilitate drainage. Unfortunately this stripping causes negative pressures which may cause further bleeding.

These chest drainage collection systems usually include several dependent loops in the drainage tube. If the entire drainage system is devoid of air spaces, the vacuum created in the collection chamber should be transmitted to the pleural and/or mediastinal spaces ensuring continuous drainage. This reduces dwell time so that residence of blood in the pleural and mediastinal spaces is insufficient to permit blood clotting. In addition, a relatively large bore drainage tube creates a relatively large volume increasing dwell time and the possibility of clotting within the tubing.

Unfortunately, the relatively large bore of the drainage tubing creates a siphon break due to the inability to hold a column of liquid against gravity. In order to keep the downhill column filled with liquid, the internal diameter should be reduced. Proper sizing of the drainage tubing ensures that "uphill legs" do not cancel the negativity created by the vacuum. The pleural and/or mediastinal spaces, therefore, have the negative value imposed by the vertical height difference between the catheter tip and the point where the drainage tube enters the collection chamber except while there is actual flow in the collection tubing.

Typically such drainage systems include at least two chambers comprising blood reservoir disposed in series, where the first when full overflows into the second. Usually the first chamber has a smaller cross-section so that volumes can be read more accurately. If this is intended to serve and purpose, this purpose is defeated once the first chamber is full and further readings have to be made in the larger less accurate second chamber.

U.S. Pat. No. 3,363,626 and U.S. Pat. No. 3,363,627 describe in detail the anatomical and physiological environs in which such devices are employed as well as the earliest designs of "threebottle" drainage systems.

Specifically, U.S. Pat. Nos. 3,363,626 and 3,363,627 each discloses an underwater drainage apparatus comprising a unitary device having a collection chamber, underwater seal chamber and pressure regulating manometer chamber including an underwater seal saver to prevent the loss of the underwater seal during conditions of high negativity in a patient's pleural and/or mediastinal cavities.

U.S. Pat. No. 3,559,647 relates to an underwater drainage apparatus including a trap chamber, underwater seal chamber and pressure regulating manometer chamber. A baffle arrangement is provided to prevent loss of liquid from the underwater seal chamber and/or the pressure regulator chamber. A fluid flow meter is provided for measuring air flow through the underwater seal chamber and/or through the pressure regulator chamber.

U.S. Pat. No. 3,683,913 discloses an underwater drainage apparatus for evacuating fluids from body cavities comprising a integrally formed collection chamber, underwater seal chamber and pressure regulating manometer chamber. Air flow meters are disposed in the underwater seal chamber and the pressure regulating chamber to measure gas flow. A valve is provided between the underwater seal and the collection chamber preventing high negative pressures from being developed in the pleural cavity.

U.S. Pat. No. Re. 29,877 of U.S. Pat. No. 3,853,128 shows a drainage apparatus for evacuating fluids from cavities including a collection chamber for collecting fluids from a body cavity, a water seal chamber and a pressure regulator chamber. A valve mechanism is provided in the water seal chamber to permit the outflow of gases from the apparatus in the event of a sudden increase in pressure in the device resulting from respiratory movements or leakage of air.

U.S. Pat. No. 4,443,220 relates to a blood collection and transfer apparatus for autotransfusion in preoperative, operative and postoperative procedures.

Other examples of the prior art are found in U.S. Pat. No. 3,782,497 and U.S. Pat. No. 4,258,824.

Unfortunately such devices commonly permit blood clotting in the mediastinal or pleural spaces due to irregular drainage. In addition, the monitoring of continuous flow rates are not accurate.

SUMMARY OF THE INVENTION

The present invention relates to a liquid collection device for use with various surgical procedures to control and monitor the rate of liquid flow of liquid from body cavities such as the pleural and/or mediastinal cavities of a patient.

The liquid control device comprises a liquid collection housing operatively housing a liquid collection section and pressure control/liquid isolation section. An opening and handle are formed on the upper mid-portion of the liquid collection housing.

The liquid collection section comprises an upper liquid flow rate monitoring chamber and lower liquid accumulation reservoir. A fluid outlet feed apparatus is partially disposed within the upper liquid flow rate monitoring chamber. The upper liquid flow rate monitoring chamber includes an inlet and outlet port coupled to the pleural and/or mediastinal cavities and lower liquid accumulation reservoir respectively through an inlet fluid conduit and outlet fluid conduit respectively. The lower liquid accumulation reservoir includes an inlet and outlet port coupled to the upper liquid flow rate monitoring chamber and pressure control/liquid isolation section respectively through the outlet fluid conduit and an inlet vacuum conduit respectively.

The pressure control/liquid isolation section comprises a pressure control chamber and liquid isolation chamber coupled to the liquid collection section and a vacuum source through a gas inlet port and vacuum suction port respectively. The pressure control chamber comprises a first and second liquid isolation chamber column disposed in fluid communication relative to each other through a lower liquid isolation chamber port. The liquid isolation chamber comprises a first and second liquid isolation chamber column disposed in fluid communication relative to each other through a lower liquid isolation chamber port. The pressure control chamber and liquid isolation chamber are formed in open fluid communication relative to each other through an upper vacuum chamber port; while, the pressure control chamber is formed in open fluid communication with the atmosphere through an atmosphere port.

In use the inlet fluid conduit is coupled to the pleural and/or mediastinal cavities by a drainage catheter inserted substernally. The vacuum source is then activated. Typically, a vacuum of approximately 20 centimeters of water is created resulting in a liquid level differential before the first and second vacuum chamber column to allow sufficient vacuum to be established in the liquid collection device. The amount of vacuum is visually shown by a vacuum window and vacuum indicia formed on the liquid collection housing.

So configured, excess fluids including gases and liquids will begin to flow from the pleural and/or mediastinal cavities and through the inlet fluid conduit into the upper liquid flow rate monitoring chamber through the inlet port. Gases are drawn from the upper liquid flow rate monitoring chamber through the lower liquid accumulation reservoir and liquid isolation chamber to the vacuum suction port and exhausted therefrom. The passage of these gases through the water in the second isolation chamber column causes the water to bubble providing a visual indication through a liquid isolation window formed in the liquid collection housing.

When the upper liquid flow rate monitoring chamber is full, the entire volume of blood is siphoned to the lower liquid accumulation chamber by the fluid outlet feed apparatus. The liquid levels within the upper liquid flow rate monitoring chamber and lower liquid accumulation chamber are visable through a liquid flow rate window and liquid accumulation window respectively formed in the liquid collection housing.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which:

FIG. 4 is a side view of the inlet fluid conduit, inlet feed spout and two position valve means.

FIG. 5 is a top view of the inlet fluid conduit, inlet feed spout and two position valve means.

FIG. 6 is a cross-sectional view of the vacuum conduit and restrictor.

Similar reference characters refer to similar parts throughout the several views of the drawings.

DETAILED DESCRIPTION OF THE PREFERRED EMBODIMENT

Figure 1:
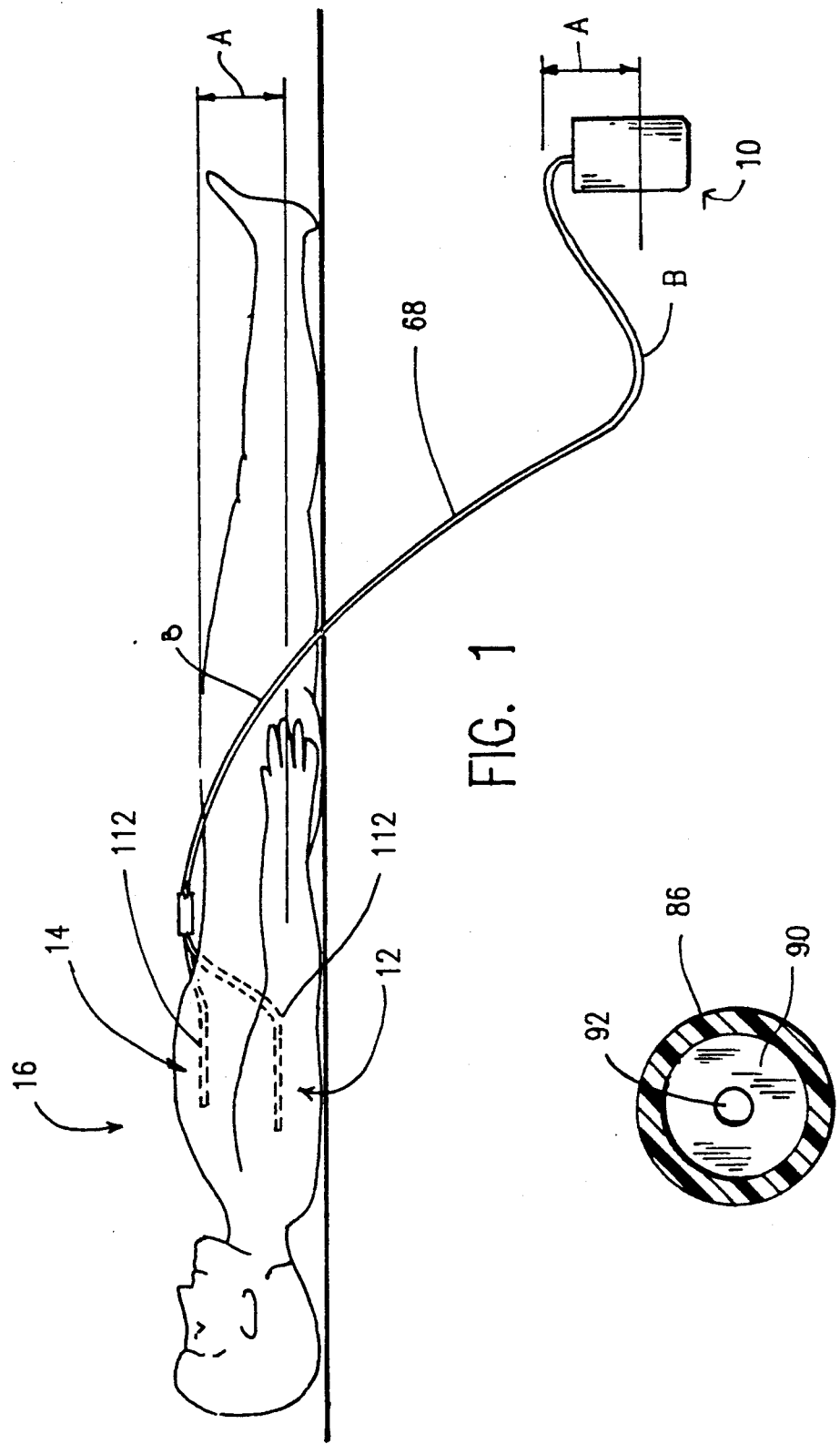
FIG. 1 is a view of the liquid collection device in use.

As shown in FIG. 1, the present invention relates to a liquid collection device generally indicated as 10 for use with various surgical procedures to control and monitor the rate of flow of liquid from one or more body cavities such as the pleural and/or mediastinal cavities indicated as 12 and 14 respectively of a patient 16.

Figure 2:
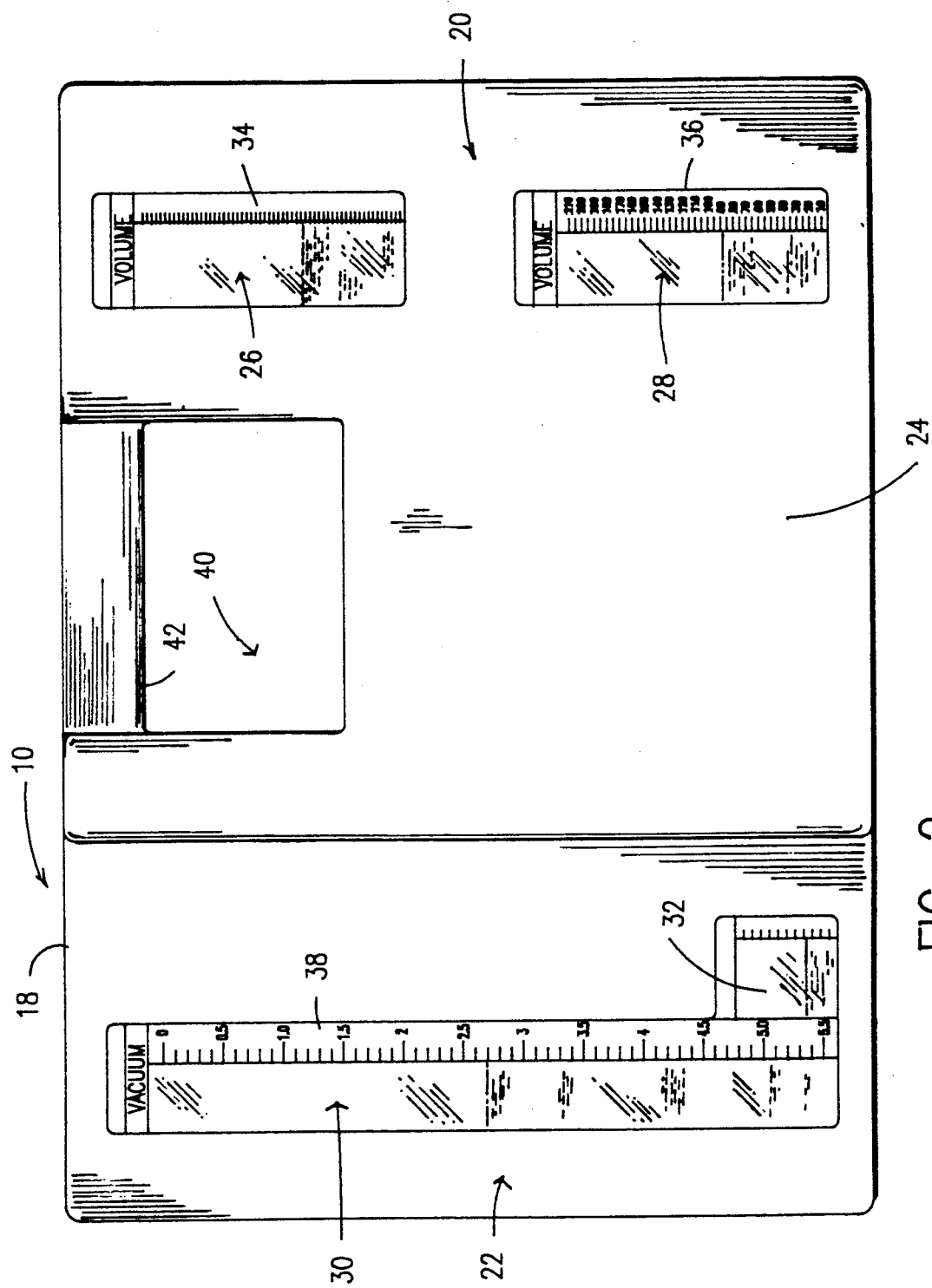
FIG. 2 is a front detailed view of the liquid collection device.
Figure 3:
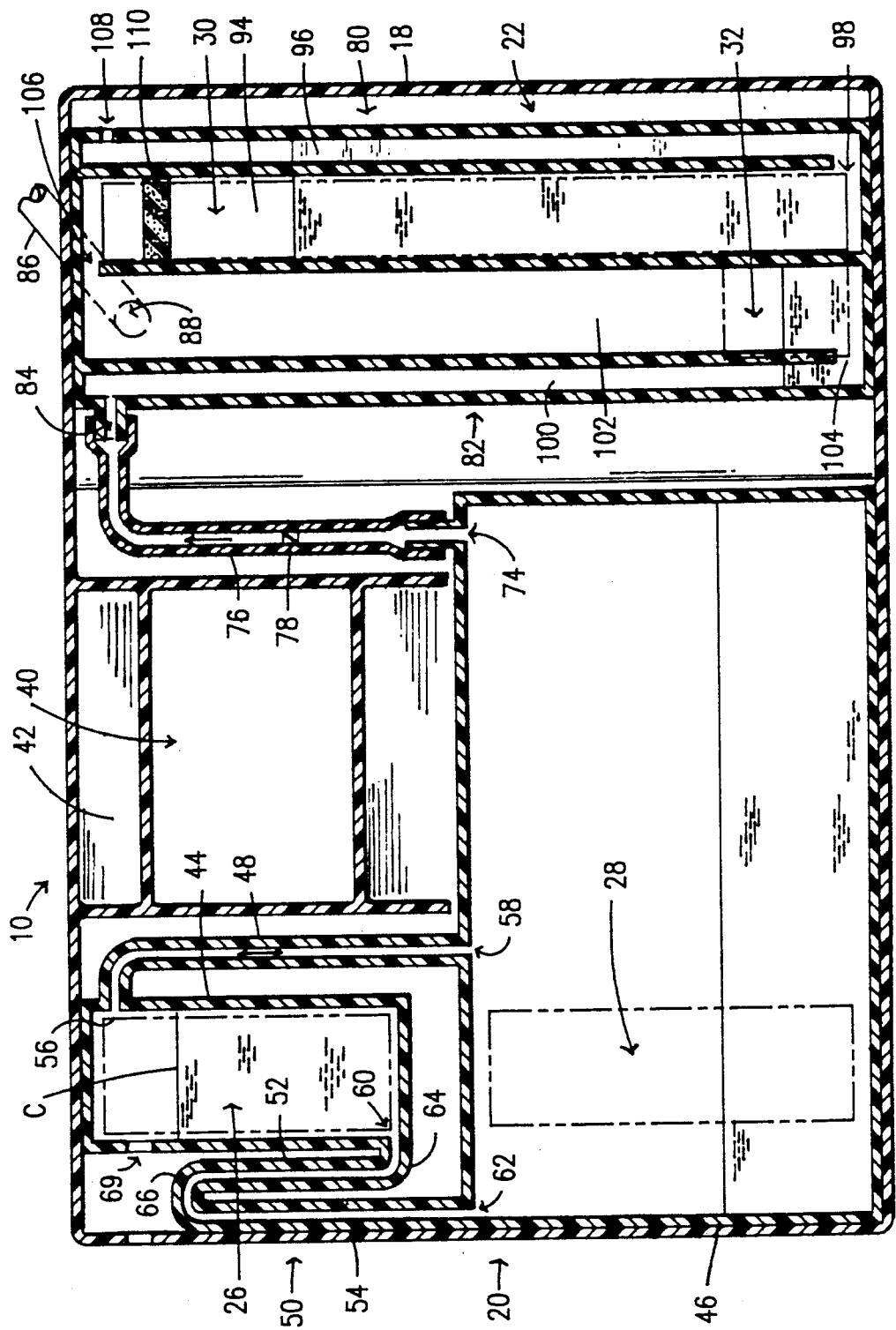
FIG. 3 is a rear cross-sectional view of the liquid collection device.

As shown in FIGS. 2 and 3, the liquid collection device 10 comprises a liquid collection housing 18 operatively housing a liquid collection section and pressure control/liquid isolation section generally indicated as 20 and 22 respectively. The front panel 24 of the liquid collection housing 18 includes a liquid flow rate window 26, liquid accumulation window 28, vacuum window 30 and liquid isolation window to provide a visual indication of the liquid flow rate, volume of liquid accumulated, amount of vacuum created within the liquid collection device 10 and gas flow from the liquid collection section 20 respectively. A liquid flow rate indicia or scale 34, liquid accumulation indicia or scale 36 and vacuum indicia or scale 38 are disposed adjacent the liquid flow rate window 26, liquid accumulation window 28 and vacuum window 30 respectively to provide a quantitive indication of the liquid flow rate, volume of blood accumulation and vacuum respectively. An opening 40 and handle 42 are formed on the upper mid-portion of the liquid collection housing 18.

As shown in FIG. 3, the liquid collection section 20 comprises an upper liquid flow rate monitoring chamber 44 and lower liquid accumulation reservoir.

A fluid outlet feed apparatus is coupled between the upper liquid flow rate monitoring chamber 44 and lower liquid accumulation reservoir 46 to dynamically feed a predetermined volume of liquid from the upper liquid flow rate monitoring chamber 44 to the lower liquid accumulation reservoir 46. The fluid outlet feed apparatus comprises an air vent tube 48 and a liquid feed tube generally indicated as 50 including a first and second liquid feed leg indicated as 52 and 54 respectively. The air vent tube 48 is coupled to the upper flow rate monitoring chamber 44 and lower liquid accumulation reservoir 46 through a first air vent port 56 and second air vent port 58 respectively. The liquid feed tube 50 is coupled to the upper flow rate monitoring chamber 44 and lower liquid accumulation reservoir 46 through a first liquid port 60 and second liquid port 62 respectively. A lower arcuate loop 64 extends between the first liquid port 60 formed in the bottom of the upper liquid flow rate monitoring chamber 44 and the first liquid feed leg 52; while, an upper arcuate loop 66 extends between the upper ends of the first and second liquid feed legs 52 and 54. It should be noted that the cross-sectional area of the first liquid feed leg 52 is greater than the cross-sectional area of the second liquid feed leg 54. The upper liquid flow rate monitoring chamber 44 is coupled to the patient 16 through an inlet feed conduit 68 coupled through an inlet 69 to an inlet feed spout 70 through a two position valve means 72 as best shown in FIGS. 4 and 5.

The lower liquid accumulating reservoir 46 is coupled to the pressure control/liquid isolation section 22 through a vacuum port 74 and inlet vacuum conduit 76 having a one-way check valve means 78 disposed therein to prevent liquid flowing therethrough.

As shown in FIG. 3, the pressure control/liquid isolation section 22 comprises a pressure control chamber and liquid isolation chamber generally indicated as 80 and 82 respectively coupled to the liquid collection section 20 and a vacuum source (not shown) through a gas inlet port 84 and a vacuum conduit 86 coupled to a suction port 88 respectively. As shown in FIG. 6, a restrictor 90 having a reduced orifice 92 formed therein is disposed within the vacuum conduit 86 to reduce the turbulence of air flow therethrough.

The pressure control chamber 80 comprises a first and second vacuum chamber column indicated as 94 and 96 respectively disposed in fluid communication relative to each other through a lower vacuum chamber port 98.

The liquid isolation chamber 82 comprises a first and second liquid isolation chamber column indicated as 100 and 102 respectively disposed in fluid communication relative to each other through a lower liquid isolation chamber port 104.

The pressure control chamber 80 and liquid isolation chamber 82 are formed in open fluid communication relative to each other through an upper vacuum chamber port 106; while, the pressure control chamber 80 is formed in open fluid communication with the atmosphere through an upper atmospheric port 108. A baffle or open cell sponge 110 is disposed in the upper portion of the first vacuum chamber column 94.

The inlet fluid conduit 68 comprises an inner diameter less than one-quarter of an inch and preferably three-sixteenths of an inch which in combination with the dynamic siphoning effect of the fluid outlet feed apparatus maintains the vacuum throughout the liquid collection device 10.

In use the inlet fluid conduit 68 is coupled to the pleural and/or mediastinal cavities 12 and 14 through catheters 112 placed substernally. The vacuum source (not shown) is then activated drawing air from the liquid collection device 10 creating a vacuum therein. Typically, a vacuum of approximately 20 centimeters of water is created resulting in a liquid level differential between the first vacuum chamber column 94 and second vacuum chamber column 96 to create sufficient vacuum in the liquid collection device 10 to draw blood from the pleural and/or mediastinal cavities 12 and 14. The liquid level within the first vacuum chamber column 94 represents the vacuum visually shown through the vacuum window 30 and the value of which is indicated by the vacuum indica 38.

With the two position valve means 72 in the first position, excess fluids including gas and liquid flow from the pleural and/or mediastinal cavities 12 and 14 through the inlet fluid conduit 68 into the upper liquid flow rate monitoring chamber 40 through the inlet feed spout 70. Gas is drawn from the upper liquid flow rate monitoring chamber 44 through the lower liquid accumulation reservoir 46 to the liquid isolation chamber 82. The passage of this gas through the liquid in the second liquid isolation chamber column 102 causes the liquid therein to bubble providing a visual indication through the liquid isolation window 32 of the gas flow from the liquid collection section 20.

Blood present in the pleural and/or mediastinal cavities 12 and 14 is drawn under vacuum through the inlet fluid conduit 68 into the upper liquid flow rate monitoring chamber 44. Once the inlet fluid conduit 68 is filled with blood, the vacuum created within the liquid collection device 10 will maintain the liquid throughout the inlet fluid conduit 68 despite the uphill legs A. The volume of blood within the upper liquid flow rate monitoring chamber 44 is visable through the liquid flow rate window 26. The time/volume relationship of blood accumulation in the upper liquid flow rate monitoring chamber 44 as seen through the liquid flow rate window 26 as quantified by the liquid flow rate indicia provides a blood flow rate measure. In addition, blood droplets fed from the inlet feed spout 70 corresponding to the patient's 16 bleeding are visable through the liquid flow rate window 26.

When the blood in the upper liquid flow rate monitoring chamber 44 reaches level C, the entire volume of blood is siphoned to the lower liquid accumulation reservoir 46 by the fluid outlet feed apparatus. The volume of blood collected in the lower liquid accumulation reservoir 46 is visable through the liquid accumulation window 28. A visual measure of the blood accumulation in the lower liquid accumulation reservoir 46 is provided by the liquid accumulation indicia 36.

It should be noted that once the vacuum is established and blood flow initiated, the vacuum source (not shown) may be deactivated.

The unique combination of the reduced diameter of the inlet fluid conduit 68 and structure of the fluid outlet feed apparatus provides a sustained, continuous flow of blood from the pleural and/or mediastinal cavities 12 and 14 providing an accurate depiction of patient bleeding and avoiding accumulation of blood within the pleural and/or mediastinal cavities 12 without the necessity of milking or stripping of the inlet fluid conduit 68.

When the two position valve means 72 is in the second position excess fluids flow from the pleural and/or mediastinal cavities 12 and 14 through the inlet fluid conduit 68 and the two position valve means 72 to a blood collection bag (not shown).

It is envisioned that the blood contacting surfaces throughout the drainage system and liquid collection device 10 may contain an anticoagulant material.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A liquid collection device for use with various surgical procedures to control and monitor the rate of flow of liquid from body cavity such as the pleural cavity comprising a liquid collection section including an upper liquid flow rate monitoring chamber to be coupled to the body cavity by an inlet fluid conduit and a lower liquid accumulation reservoir in fluid communication therewith, a fluid outlet feed apparatus coupled between said upper liquid flow rate monitoring chamber and said lower liquid accumulation reservoir to dynamically feed a predetermined volume of liquid to said lower liquid accumulation reservoir when said predetermined volume of liquid is received in said upper liquid flow rate monitoring chamber, said fluid outlet feed apparatus comprising an air vent tube coupled between said upper liquid flow rate monitoring chamber and said lower liquid accumulation reservoir through a first and second air vent port respectively and a liquid feed tube coupled to said upper liquid flow rate monitoring chamber and said lower liquid accumulation reservoir through a first and second liquid port respectively.

2. The liquid collection device of claim 1 wherein said liquid feed tube comprises a first liquid feed leg coupled to said first liquid port and a second liquid feed leg coupled to said second liquid port.

3. The liquid collection device of claim 2 wherein said liquid feed tube further includes a lower arcuate loop coupled between said first liquid port and said first liquid feed leg and an upper arcuate loop coupled between said first liquid feed leg and said second liquid feed leg.

4. The liquid collection device of claim 3 wherein said first liquid port is formed in the bottom of said upper liquid flow rate monitoring chamber.

5. The liquid collection device of claim 3 wherein said first air vent port is disposed in the horizontal plane above said upper arcuate loop.

6. The liquid collection device of claim 2 wherein the cross-sectional area of said first liquid feed leg is greater than the cross-sectional area of said second liquid feed leg.

7. The liquid collection device of claim 1 further including a pressure control/liquid isolation section including a pressure control chamber for containing a predetermined volume of liquid therein open to the atmosphere through an atmospheric port and a liquid isolation chamber for containing a second volume of liquid in fluid communication with said lower fluid accumulation reservoir through a port, inlet vacuum conduit and gas inlet port and to said pressure control chamber through an upper vacuum chamber port, said pressure control liquid isolation section further including a suction port adapted to be coupled to a vacuum source through a vacuum conduit to control the flow of liquid from the body cavity through said inlet fluid conduit at a predetermined pressure to permit flow of gas from said lower liquid accumulation reservoir to said liquid isolation chamber in proportion to gas received in said liquid collection section from the body cavity.

8. The liquid collection device of claim 7 further including a one-way check valve disposed in said inlet vacuum conduit to prevent the flow of liquid therethrough.

9. The liquid collection device of claim 7 further including a liquid collection housing to operatively house said liquid collection section and said pressure control/liquid isolation section.

10. The liquid collection device of claim 9 wherein said liquid collection housing includes a front panel having a liquid flow window formed therein to provide a visual indication of the liquid flow to said upper liquid flow rate monitoring chamber.

11. The liquid collection device of claim 10 wherein said front panel further includes a liquid flow rate indicia formed adjacent said liquid flow windows to provide a visual measure of liquid accumulated in said upper liquid flow rate monitoring chamber.

12. The liquid collection device of claim 10 further including a liquid accumulation window formed in said front panel to provide a visual indication of liquid accumulation in said lower liquid accumulation reservoir.

13. The liquid collection device of claim 12 wherein said front panel further includes a liquid accumulation indicia formed adjacent said liquid accumulation window to provide a visual measure of liquid accumulated in said lower liquid accumulation reservoir.

14. The liquid collection device of claim 10 further including a vacuum window formed in said front panel to provide a visual indication of vacuum formed in said liquid collection device.

15. The liquid collection device of claim 14 wherein said front panel further includes a vacuum indicia to provide a visual measure of the vacuum formed in said liquid collection device.

16. The liquid collection device of claim 10 further including a liquid isolation window to provide a visual indication of gas flow from said liquid collection section.

17. The liquid collection device of claim 9 wherein said liquid collection housing includes a handle formed thereon.

18. The liquid collection device of claim 7 further including a restrictor having a reduced orifice formed therethrough disposed within said vacuum conduit to reduce the turbulence of air flow therethrough.

19. The liquid collection device of claim 1 wherein the inside diameter of said inlet fluid conduit is less than one-quarter of an inch.

20. The liquid collection device of claim 19 wherein the inside diameter of said inlet fluid conduit is substantially three-sixteenths of an inch.

* * * * *